(12) United States Patent
Kennedy et al.

(10) Patent No.: US 10,546,114 B2
(45) Date of Patent: Jan. 28, 2020

(54) SELF-AUTHENTICATING INTRAVASCULAR DEVICE AND ASSOCIATED DEVICES, SYSTEMS, AND METHODS

(71) Applicant: Koninklijke Philips N.V., Eindhoven (NL)

(72) Inventors: Timothy J. Kennedy, San Diego, CA (US); David Sprague, San Diego, CA (US); Jason Y. Sproul, Watertown, MA (US); Andreas Johansson, Wayland, MA (US); Francis Harrington, San Diego, CA (US); Derek Bruce Eldridge, Tyngsboro, MA (US); Todd Bitner, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 827 days.

(21) Appl. No.: 14/722,600

(22) Filed: May 27, 2015

(65) Prior Publication Data
US 2015/0347744 A1   Dec. 3, 2015

Related U.S. Application Data

(60) Provisional application No. 62/003,447, filed on May 27, 2014.

(51) Int. Cl.
*A61B 1/04* (2006.01)
*G06F 21/44* (2013.01)
(Continued)

(52) U.S. Cl.
CPC .............. *G06F 21/44* (2013.01); *A61B 5/026* (2013.01); *A61B 5/0066* (2013.01); *A61B 5/0215* (2013.01); *A61B 8/12* (2013.01)

(58) Field of Classification Search
CPC ......... A61B 5/06; A61B 5/0066; A61B 5/026; A61B 5/0215
See application file for complete search history.

(56) References Cited

U.S. PATENT DOCUMENTS

2002/0010432 A1   1/2002  Klitmose
2004/0087832 A1   5/2004  Glukhovsky et al.
(Continued)

OTHER PUBLICATIONS

Korean Intellectual Property Office, International Search Report for PCT/US2015/032562 dated Jul. 24, 2015, 14 pages.

*Primary Examiner* — Michael J D Abreu

(57) ABSTRACT

A method of authorizing a limited use intravascular device can include determining if the intravascular device is in communication with a clinical system; determining if the intravascular device is authorized for clinical operation without providing the clinical system access to intravascular device data stored on the intravascular device; and providing an authorization signal to the clinical system. An intravascular device can include a flexible elongate member including a sensing component at a distal portion and a connector at a proximal portion, the connector including: a memory component configured to store a parameter value; a processing component; and a charge storage component configured to power the memory component and/or the processing component; wherein the processing component is configured to determine if the flexible elongate member is authorized for clinical operation using the parameter value without providing the parameter value to a clinical system.

20 Claims, 6 Drawing Sheets

(51) Int. Cl.
  *A61B 5/026*     (2006.01)
  *A61B 5/00*      (2006.01)
  *A61B 5/0215*    (2006.01)
  *A61B 8/12*      (2006.01)

(56) References Cited

U.S. PATENT DOCUMENTS

| | | |
|---|---|---|
| 2005/0108057 A1 | 5/2005 | Cohen et al. |
| 2006/0129140 A1 | 6/2006 | Todd et al. |
| 2007/0083111 A1 | 4/2007 | Hossack et al. |
| 2007/0106208 A1* | 5/2007 | Uber, III ............... A61M 5/142 604/65 |
| 2009/0043253 A1 | 2/2009 | Podaima |
| 2011/0037876 A1 | 2/2011 | Talbert et al. |
| 2011/0270091 A1 | 11/2011 | Hossack et al. |
| 2011/0282671 A1 | 11/2011 | Dicks et al. |
| 2012/0016299 A1* | 1/2012 | Caffey ............... A61M 5/14276 604/96.01 |
| 2012/0065469 A1 | 3/2012 | Allyn et al. |
| 2012/0265189 A1* | 10/2012 | Davis ................... A61B 18/02 606/22 |
| 2013/0190646 A1 | 7/2013 | Weinstein et al. |

* cited by examiner

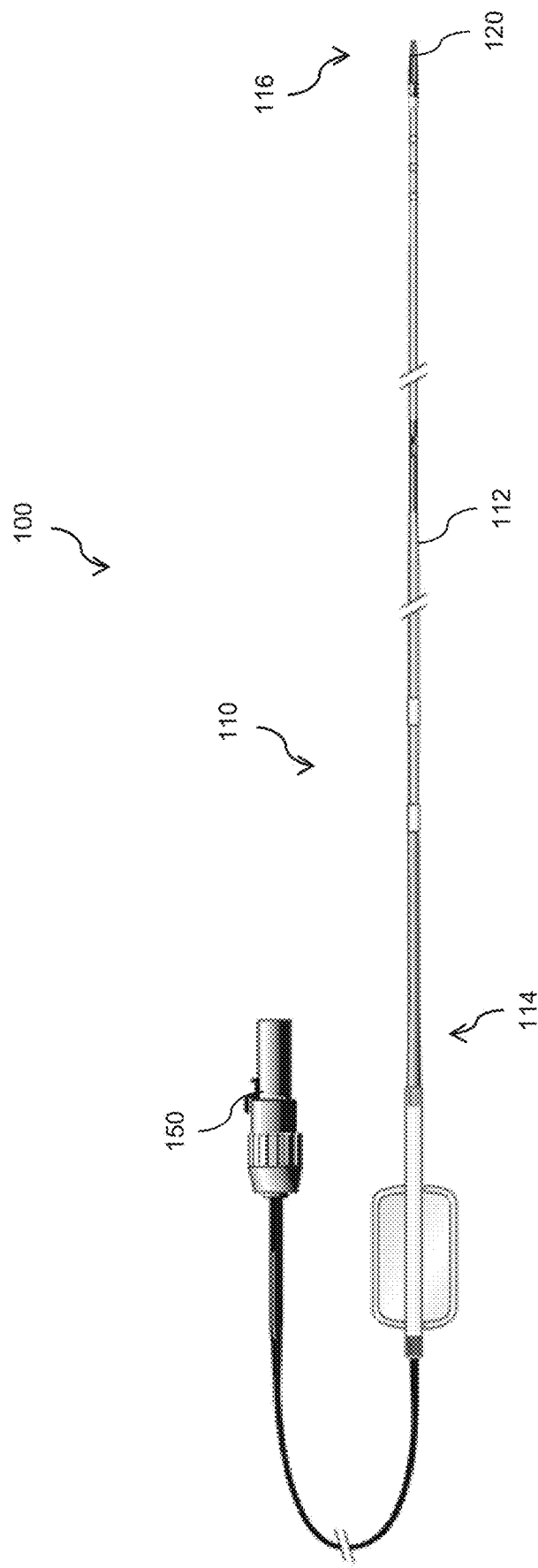

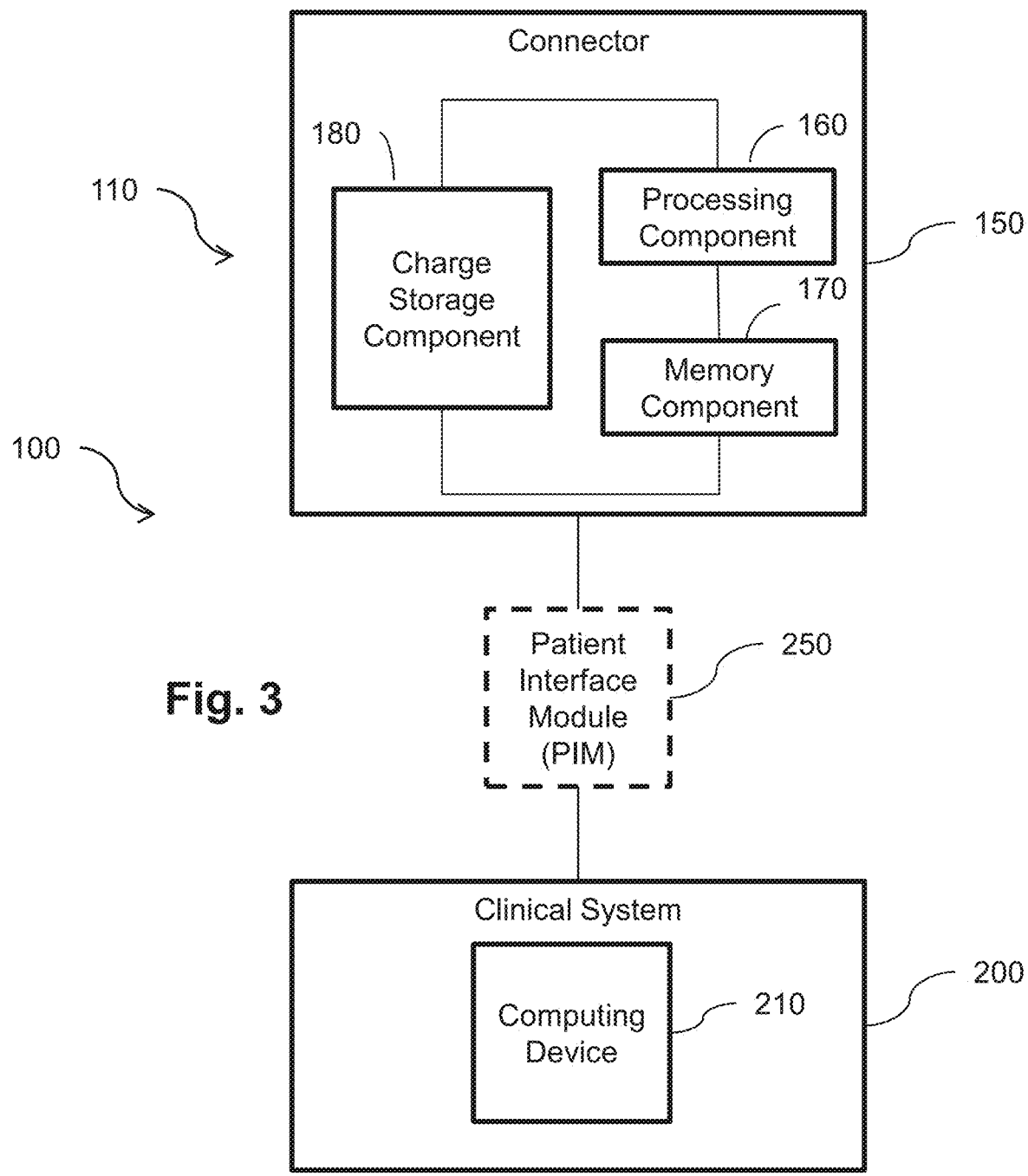

SELF-AUTHENTICATING INTRAVASCULAR DEVICE AND ASSOCIATED DEVICES, SYSTEMS, AND METHODS

CROSS REFERENCE TO RELATED APPLICATIONS

The present application claims priority to and the benefit of the U.S. Provisional Patent Application No. 62/003,447, filed May 27, 2014, which is hereby incorporated by reference in its entirety.

TECHNICAL FIELD

The present disclosure relates generally to intravascular devices including a logic device that implements an authentication algorithm to determine if the intravascular device can be safely used in a clinical procedure.

BACKGROUND

Intravascular devices, such as guide wires, catheters, guide catheters, etc., can be configured for imaging, flow measurement, pressure measurement, and/or providing therapy, among other functions. Such intravascular devices are generally disposable devices. Further, a manufacturer generally rates the intravascular device for a single use. The intravascular devices can be required to be sterile and/or have consistent performance at or near the limits of material properties, such as the plastic-elastic limit. Thus, the manufacturer can guarantee the safety of the intravascular device and/or the integrity of the data collected using the intravascular device only for a single use. After being used within the vasculature of a patient in a clinical procedure, the intravascular device is discarded.

Recently, third parties who do not have support from the original equipment manufacturer have collected used intravascular devices. The used intravascular devices are then sterilized, repackaged, and sold for future use in clinical procedures. The third parties can lack the manufacturer's understanding of the design, tolerances, limitations, verification and validation data, manufacturing process controls, calibrations, and other aspects of the intravascular devices. Accordingly, there are significant risks to patients when unauthorized intravascular devices are used. This is true even if sterility, bio-burden, and biocompatibility are validated according to established standards and regulations. The intravascular devices cannot be guaranteed or expected to meet the efficacy standards of an authentic intravascular device from the manufacturer. When an intravascular device is incorrectly reprocessed or reused, patients can be exposed to direct harm via contamination. It can also expose patients to the possibility of misdiagnosis when a disposable intravascular device is used for a longer time than it was designed to operate safely. In addition to patient safety concerns, a manufacturer also suffers financial losses when customers purchase repackaged, used intravascular devices as opposed to authorized ones.

Some efforts have been made previously to ensure that only authorized intravascular devices are used in clinical procedures. Disposable intravascular devices are connected to a reusable computing device in the procedure room before they are used. The computing device can conduct one or more checks to verify the authenticity of the intravascular device. When the intravascular device's on-board data does not pass the check, the computing device can cease operating or can disallow use of the intravascular device. Conventionally, the computing device must access to the intravascular device data in order for the check to be conducted. Thus, if a computing device has not been programmed to conduct the check before being deployed in a clinical environment, the computing device may be unable to verify the authenticity of intravascular devices.

Thus, there remains a need for an authentication system that comprehensively prevents the use of unauthorized, fraudulent, and/or otherwise tampered-with intravascular devices.

SUMMARY

Embodiments of the present disclosure provide a self-authenticating intravascular device, such as a guide wire or catheter. The intravascular device can include a logic device that can determine if the intravascular device is authorized to be used in a clinical procedure. The intravascular device can be self-authenticating in that intravascular device can make the determination of whether it is authorized for clinical use on its own. The clinical system to which the intravascular device is connected need not make the determination, and intravascular device data stored on the intravascular device need not be provided to the clinical system.

In an exemplary aspect, the present disclosure is directed to method of authorizing a limited use intravascular device. The method includes determining if the intravascular device is in communication with a clinical system; determining, when the intravascular device is in communication with the clinical system, if the intravascular device is authorized for clinical operation without providing the clinical system access to intravascular device data stored on the intravascular device; and providing an authorization signal to the clinical system when it is determined that the intravascular device is authorized for clinical operation.

In another exemplary aspect, the present disclosure is directed to an intravascular device. The device includes a flexible elongate member including a sensing component at a distal portion and a connector at a proximal portion, the connector configured to provide direct or indirect communication with a clinical system, the connector including: a memory component configured to store a parameter value; a processing component in communication with the memory component; and a charge storage component configured to power at least one of the memory component and the processing component; wherein the processing component is configured to determine if the flexible elongate member is authorized for clinical operation by determining if the parameter value is greater than or less than a threshold value without providing the parameter value to the clinical system.

In another exemplary aspect, the present disclosure is directed to an intravascular system. The system includes an intravascular device comprising a flexible elongate member having a sensing component at a distal portion and a connector at a proximal portion, the limited use intravascular device further including: a memory component configured to store a parameter value; a processing component configured to determine if the intravascular device is authorized for clinical use based on the parameter value; and a charge storage component configured to power at least one of the memory component and the processing component; a clinical system comprising a computing device in direct or indirect communication with the intravascular device; wherein the processing component is configured to determine if the intravascular device is authorized for clinical operation without allowing the clinical system to access the memory component; and wherein the clinical system is configured to allow or disallow the clinical operation of the intravascular device in response to a signal received from the intravascular device representative of the determination by the processing component as to whether the intravascular device is authorized for clinical operation.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 1 is a diagrammatic schematic view of an intravascular system according to aspects of the present disclosure.

FIG. 3 is a block diagram of an intravascular system according to aspects of the present disclosure.

DETAILED DESCRIPTION

Figure 2A:
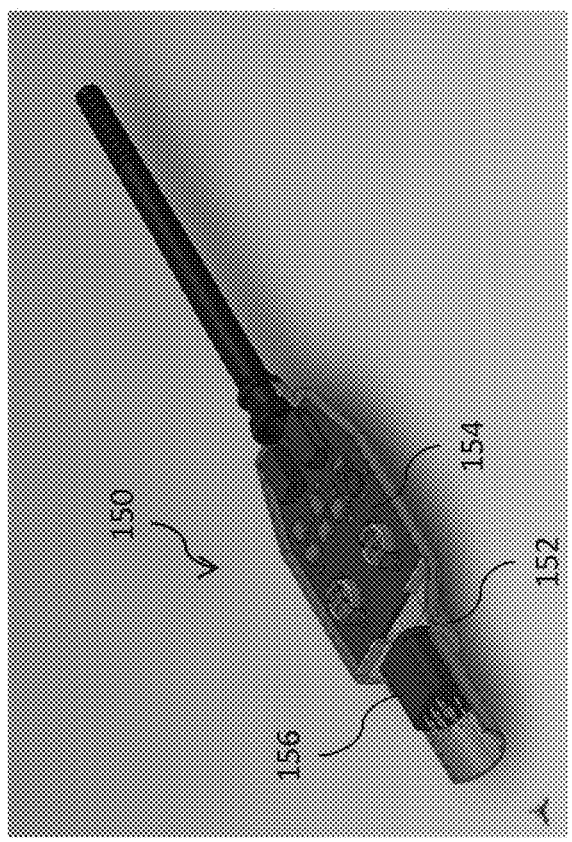
FIG. 2a is a perspective view of a connector of an intravascular device according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The devices, systems, and methods described herein relate to a self-authenticating intravascular device. The intravascular device can include a connector having a processing component. The processing component can be configured to determine if the intravascular device authorized for clinical use. The processing component can make the determination by tracking a parameter maintained by the intravascular device itself. Though the intravascular device can be in communication with a clinical system, the clinical system need not make the determination of whether the intravascular device is authorized for clinical use, and the clinical system need not be provided intravascular device data to make that determination.

Patient safety can be improved by utilizing the self-authenticating intravascular device of the present disclosure. When risk of harm to the patients exists from unauthorized use of the intravascular device, the intravascular device can stop itself from operating or cause the clinical system to stop the intravascular device from operating. The self-authenticating logic described herein can be implemented in clinical systems already deployed in clinical environments that are not configured to conduct checked to verify the authenticity of intravascular devices. This is because the intravascular device alone can determine if it is authorized for clinical use. Thus, the costs associated with implementing changes to clinical systems already deployed in clinical environments can be avoided. Providing the logic described herein on one component can also make the intravascular device more secure by making it more difficult to bypass the logic. Implementing the logic on one component can also be more tamper resistant and more cost effective for a manufacturer to produce.

The devices, systems, and methods described herein can apply to any disposable or limited use intravascular device, including devices configured for intravascular ultrasound (IVUS), optical coherence tomography (OCT), forward-looking IVUS (FLIVUS), forward-looking intra-cardiac echo (FLICE), flow measurements, pressure measurements, and/or combinations thereof.

FIG. 1 is a diagrammatic schematic view of an intravascular system 100 according to aspects of the present disclosure. Additional components of the intravascular system 100 are illustrated in FIG. 3. The intravascular system 100 can include an intravascular device 110 that is configured to be inserted into the vasculature of the patient. The intravascular device can be a guide wire, catheter, guide catheter, etc. The intravascular device 110 can be a limited use or disposable device. The intravascular device 110 can be configured to image a lumen of a blood vessel using one or more imaging modalities (e.g., IVUS, OCT, etc.). The intravascular device 110 can be configured to measure the pressure and/or flow of blood through the blood vessel. The intravascular device 110 can include a flexible elongate member 112 including a proximal portion 114 and a distal portion 116. One or more components 120 for imaging, pressure measurement, flow measurement, and/or therapy can be positioned at a distal portion 116 of the intravascular device 110. The one or more components 120 can include an IVUS imaging component, OCT imaging component, pressure transducer, etc. In some embodiments, the one or more components 120 can include therapeutic components, including ablation electrode(s), an angioplasty balloon, scoring blades, etc.

The intravascular device 110 can include a connector assembly that extends from the proximal portion 114 of the flexible elongate member 112. The connector assembly can facilitate communication between the one or more components 120 of the intravascular device 110 and a patient interface module (PIM) 250 and/or a clinical system 200 (FIG. 3). The connector assembly can include a connector or modular plug 150. The connector 150 can be configured to interface with the PIM 250 and/or the clinical system 200.

Figure 2B:
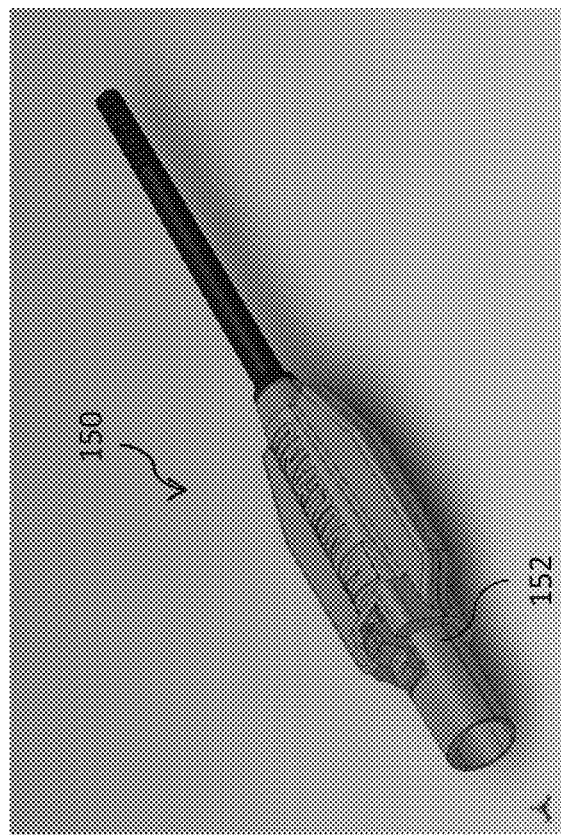
FIG. 2b is a cross-sectional perspective view of a connector of an intravascular device according to aspects of the present disclosure.

FIGS. 2a and 2b are a perspective view and a cross-sectional perspective view, respectively, of the connector 150 of the intravascular device 110 according to aspects of the present disclosure. The connector 150 can include an exterior housing or shell 152. An interior of the connector 150 can include a printed circuit board assembly (PCBA) 154. The PCBA 154 can include one or more electronic components, such as a processing component 160, a memory component 170, and/or a charge storage component 180, to execute the method steps described herein. The connector 156 can include a pin assembly 156 that directly engages the PIM 250 and/or the clinical system 200.

FIG. 3 is a block diagram of the intravascular system 100 according to aspects of the present disclosure. Additional components of the intravascular system 100 are illustrated in FIG. 1. The intravascular system 100 can include a clinical system 200. The clinical system 200 can be used in a clinical environment, along with the intravascular device 110, for intravascular imaging, pressure measurement, flow measurement, and/or therapy. The clinical system 200 can include a computing device 210 that is in communication with the intravascular device 110. The computing device can be configured to process imaging, flow measurement, and/or pressure measurement data collected by the intravascular device 110 to generate visual representations thereof. The computing device 210 can include any suitable processor, memory, and/or processing circuit for executing the methods steps described herein. The intravascular system 100 can be more generally described as a medical system, and the intravascular device 110 can be more generally described as a medical device. The intravascular components described herein are non-limiting examples. The teachings of the present disclosure can be implemented in any disposable or limited use medical device such as a transluminal and/or an endoscopic device.

The intravascular system 100 can include the PIM 250. The PIM 250 facilitates communication of signals between the clinical system 200 and the intravascular device 110. In some embodiments, the PIM 250 supplies high- and low-voltage DC power to support operation of the intravascular device 110, including the component(s) for imaging, pressure measurement, and/or flow measurement. The clinical system 200 can be in direct or indirect communication with the intravascular device 110. When the intravascular system 100 includes a PIM 250, the clinical system 200 can access the intravascular device 110 via the PIM 250. The PIM 250 can facilitate the transfer of electrical signals between the PIM 250 and the intravascular device 110. In some embodiments, the clinical system 200 can directly access the intravascular device 110. The clinical system 200 can access data collected by the one or more components 120 and/or data stored on the memory component 170. In some embodiments, the PIM 250 is configured to access, read from, and/or write to the memory component 170 based on, e.g., instructions from the clinical system 200. The clinical system 200 can be selectively brought into/out of communication with the intravascular device 110 by connecting/disconnecting the connector 150 from the PIM 250 and/or the clinical system 200.

The connector 150 of the intravascular device 110 can include any suitable processor, memory, and/or processing circuit for executing the methods steps described herein. For example, the connector 150 can include a processing component 160 in communication with a memory component 170. In some embodiments, the processing component 160 and the memory component 170 can be distinct components. In some embodiments, the processing component 160 and the memory component 170 can be an integrated component. For example, the connecter 150 can implement a combination of storage and configurable logic such as a field-programmable gate array (FPGA) or a complex programmable logic device (CPLD). The processing component 160 can include any suitable programmable logic device. The connector 150 can include various other electronic components for carrying the various steps described herein. For example, the connector 150 can include zener diode(s), oscillators, linear voltage regulator(s) such as low-dropout regulator(s) (LDO), field effect transistor(s) such as n-FETs and p-FETs, resistors, capacitor(s), etc. The various electronics components can be used, for example, to modulate the voltage transmitted to the processing component 160 and/or the memory component 170 from the charge storage component 180, the PIM 250, and/or the clinical system 200.

The processing component 160 can be configured to determine when the intravascular device 110 is brought into communication with the clinical system 200 (e.g., when the connector 150 is connected to PIM 250 and/or the clinical system 200). For example, the processing component 160 can detect when power is being provided to the intravascular device 110 by the PIM 250 and/or the clinical system 200. The processing component 160 can be configured to communicate with the clinical system 200. For example, the processing component 160 can receive a prompt from the clinical system 200 inquiring about the identity of the intravascular device 110. The prompt can be received as part of a routine start up procedure when the intravascular device 110 is brought into communication with the clinical system 200. The prompt received from the clinical system 200 can also inquire whether intravascular device 110 is authorized for clinical operation. As described herein, the processing component 160 can be configured to determine if the intravascular device 110 is authorized for clinical operation without providing the clinical system 200 access to intravascular device data stored on the intravascular device 110. The processing component 160 can provide a response (e.g., an authorization signal or a denial signal) to the clinical system 200 representative of the determination after it is made.

The processing component 160 and/or the clinical system 200 can be configured to interfere with routine operation of the intravascular device 110 when the processing component 160 determines that the intravascular device 110 is not authorized for clinical operation. For example, the processing component 160 can cause the intravascular device 110 to stop functioning. For example, the processing component 160 can provide a denial signal to the clinical system 200 to cause the intravascular device 110 to stop functioning. The processing component 160 can make the determination that the intravascular device 110 is unauthorized before the intravascular device 110 begins sensing, measuring, and/or therapeutic functions, such as when authentication logic is executed as the intravascular device 110 is brought into communication with the clinical system 200. The authentication logic can be executed more than once. Thus, the processing component 160 can make the determination that the intravascular device 110 is unauthorized during the intravascular device's 110 normal sensing, measurement, and/or therapeutic functions. For example, authentication logic can be executed during a startup procedure when the intravascular device 110 is connected to the clinical system 200 and/or the PIM 250 and after a predetermined time of use. In some embodiments, the authentication logic can be recurring at regular or irregular intervals.

Interference with the routine operation of the intravascular device 110 can be carried out in a manner that is safe to the patient. For example, the processing component 160 and/or the clinical system 200 can also determine what the intravascular device 110 is currently being used for when the determination that the intravascular device 110 is unauthorized for clinical operation is made. If stopping the intravascular device 110 at that time presents risk of harm to the patient, the processing component 160 and/or the clinical system 200 can allow the intravascular device 110 to continue operation until a safer time to stop operation. If no risk of harm to the patient exists, the processing component 160 and/or the clinical system 200 can stop operation of the intravascular device 110. For example, the processing component 160 and/or the clinical system 200 can stop the intravascular device 110 from imaging, making pressure/flow measurements, delivering therapy (e.g., ablation), etc.

The memory component 170 can be any suitable storage device, including volatile or non-volatile memory. For example, the memory component 170 can include flash memory, erasable programmable read-only memory (EPROM), electrically erasable programmable read-only memory (EEPROM), radio-frequency identification (RFID) chip, etc. The memory component 170 can have sufficient capacity to store intravascular data, including a unique serial number, configuration information, calibration information, initial parameters, a manufacture date, performance parameters, a version number, an expiration date, system configuration settings, and other data about the intravascular device 110.

The memory component 170 can be configured to store, track, and/or otherwise maintain an intravascular device parameter. The processing component 160 can access the memory component 170 to implement the self-authentication algorithms described herein. For example, the processing component 160 can implement logic based the parameter value to determine if the intravascular device 110 is authorized for clinical use. The parameter can include an elapsed time since commencement of communication with any clinical system 200, whether the intravascular device 110 has been in communication with any clinical system 200, the number of times the intravascular device 100 has been in communication with any clinical system 200, the number of times the intravascular device 110 has collected data and/or provided therapy, etc.

The connector 150 can include a charge storage component 180, such as a battery, capacitor, etc. The charge storage component 180 can be configured to power the processing component 160 and/or the memory component 170. For example, the charge storage component 180 can be configured to supplement or replace the power provided to the intravascular device by the clinical system 200 and/or the PIM 250. For example, the charge storage component 180 can provide power to the processing component 160 and/or the memory component 170 while the intravascular device 110 is not in communication with the clinical system 200. Thus, the memory component 170 can track and/or maintain the intravascular device parameter and/or the processing component 170 can determine if the intravascular device 110 is authorized for clinical operation while the intravascular device 110 is not in communication with the clinical system 200. In some embodiments, discharge of the charge storage component 180 can be the intravascular device parameter used in the self-authentication logic.

In some embodiments, the connector 150 does not include a memory component 170. In such embodiments, the processing component 160 can implement logic to determine if the intravascular device 110 is authorized for clinical use without accessing the memory component 170. The intravascular device parameter can be aspect of the logic used to conduct the authenticity check. For example, the processing component 160 can begin a timer when the intravascular device 110 is brought into communication with the clinical system 200. The processing component 160 can maintain the timer while the intravascular device is in communication with the clinical system 200 and while the two are disconnected. The processing component 160 can determine that the intravascular device 110 is unauthorized for further clinical use at the expiration of a predetermined amount of time. Time is used as an exemplary parameter only. The processing component 160 can implement self-authentication logic using other suitable parameters such as number of uses, etc.

The processing component 160 and/or the memory component 170 can maintain and/or change various operational states for the connector 150. For example, the operational states can include an unlocked state, a locked state, an armed state, an unarmed state. For example, the processing component 160 can maintain an unlocked state and a locked state describing access or lack thereof to the memory component 170 by the PIM 250 and/or the clinical system 200. For example, the processing component 160 can maintain an armed state and an unarmed state describing when parameter value of the intravascular device 110 (e.g., a use time) is ready to be tracked, being tracked, or not being tracked. During manufacturing and testing, the connector 150 can be in a disarmed state such that a parameter value will not be tracked when the connector 150 is connected to a PIM 250, a clinical system 200, and/or a manufacturing system. During the disarmed state, the manufacturing system can have write access to, e.g., calibration and identification information stored on the memory component 170. At the end of a successful catheter test, the manufacturing system can provide a command to change the state of the connector 150 to an armed state such that the parameter value will be tracked when the connector 150 is next connected to the PIM 250 and/or the clinical system 200 (e.g., during a clinical procedure.) The connector 150 can be packaged, sterilized, and prepared for shipment to the customer while in the armed state. Once the customer has used the connector 150 (e.g., during the clinical procedure), and the parameter value has expired, the clinical system 200 can provide a signal and/or the processing component 160 can determine to change the state of the connector 150 to the locked state such the memory component 170 cannot be accessed.

Figure 4:
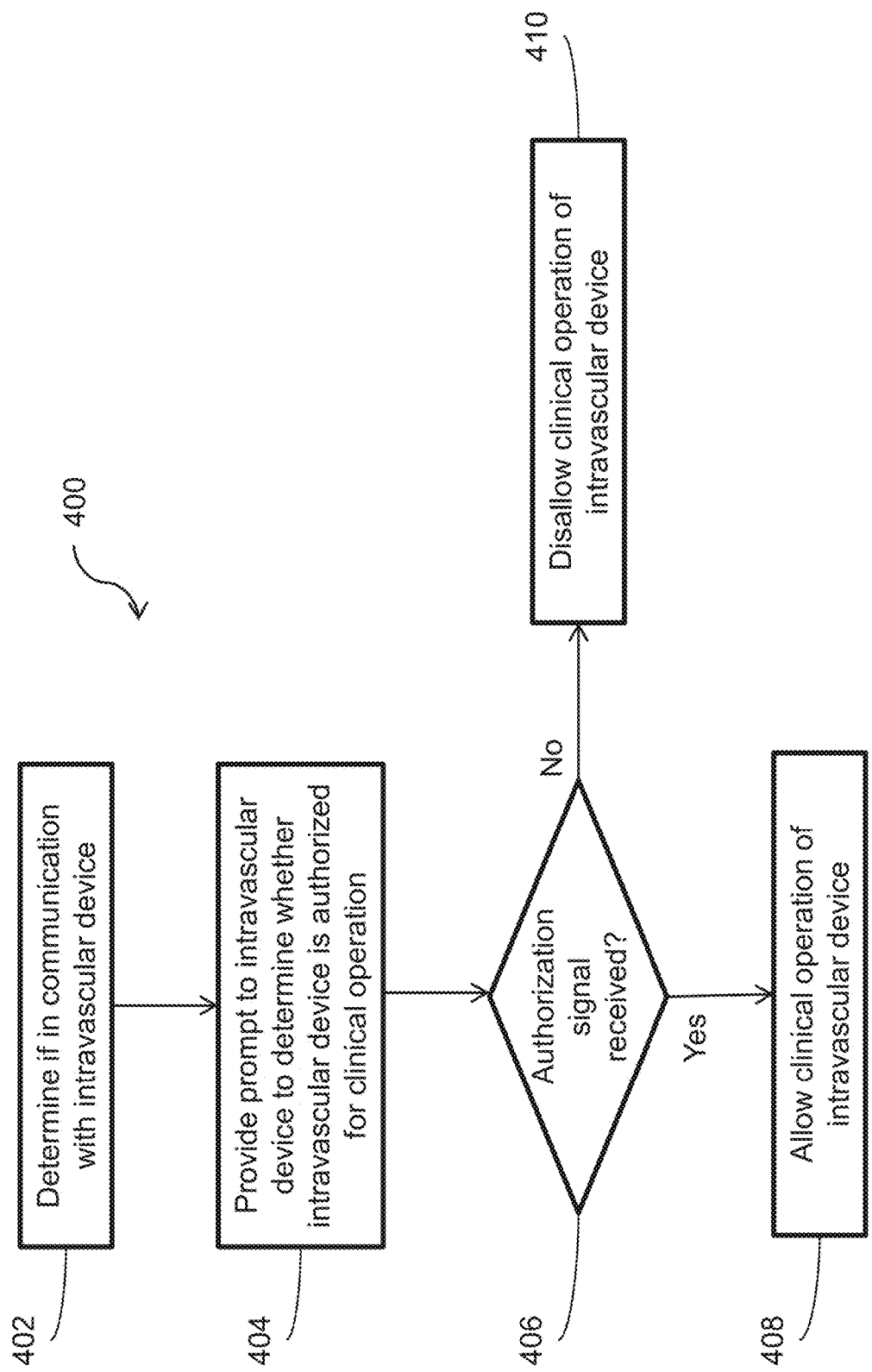
FIG. 4 is a flow diagram of a method of authorizing a limited use intravascular device using a clinical system according to aspects of the present disclosure.

FIG. 4 is a flow diagram of a method 400 of authorizing a limited use intravascular device using a clinical system 200 according to aspects of the present disclosure. One or more steps of the method 400 can be carried out by the clinical system 200 in a clinical environment. The clinical system 200 can use the method 400 to allow or disallow clinical operation of the intravascular device 110. The method 400 can be carried out when the intravascular device 110 is brought into communication with the clinical system 200 and/or various other times while the intravascular device 110 is in communication with the clinical system 200.

The method 400 can include, at step 402, determining if the intravascular device 110 is in communication with the clinical system 200. For example, the clinical system 200 can determine when the connector 150 has been plugged into or otherwise connected with the PIM 250 and/or the clinical system 200. In some embodiments, the intravascular device 110 can provide a signal indicative of connection to the clinical system 200. In some embodiments, the clinical system 150 can recognize a change in an electrical characteristic (e.g., voltage, resistance, etc.) that occurs when the connector 150 is connected. In some embodiments, an electrical circuit can be completed when the connector 150 is connected such that the clinical system 200 can provide power to the intravascular device 110. In some embodiments, the clinical system 200 can read the intravascular device data when the intravascular device 110 is brought into communication with the clinical system 200. The PIM 250 and/or the clinical system 200 can provide a signal to the connector 150 to begin tracking a parameter value as described herein when the connector 150 is brought into communication with the PIM 250 and/or the clinical system 200.

When the intravascular device 110 is in communication with clinical system 150, the method 400 can include, at step 404, providing a prompt or signal to the intravascular device 110 to determine whether the intravascular device 110 is authorized for clinical operation. In some embodiments, the clinical system 200 is not configured to and/or is not permitted by the processing component 160 to access the intravascular device 110 to determine if the intravascular device 110 is authorized for clinical operation. Thus, as described in more detail with respect to FIG. 5, the authentication logic can be executed solely by the intravascular device 110. The prompt can be sent by clinical system 200 as part of a routine startup procedure carried out when an intravascular device 110 is brought into communication with the clinical system 200. The prompt can additionally allow the clinical system 200 to determine the identity of the intravascular device 110 (e.g., guide wire or catheter, pressure-sensing or imaging, etc.).

The method 400 can include, at step 406, determining if the clinical system 150 received an affirmative response or an authorization signal from the intravascular device 110. For example, the processing component 160 can determine that the intravascular device 110 is authorized for clinical operation and provide the authorization signal indicative of the determination to the clinical system 150. When an affirmative response is received, the method 400 can include, at step 408, allowing clinical operation of the intravascular device 110. For example, the clinical system 200 can access the intravascular device data and control the intravascular device 110 for sensing, measuring, and/or therapeutic functions. When no response or a denial signal is received from the intravascular device 110, the method 400 can include disallowing clinical operation of the intravascular device 110. For example, when the processing component 160 determines that the intravascular device 110 is unauthorized for clinical operation, the processing component 160 can fail to present itself to the clinical system 200 by not responding to the prompt from the clinical system 200. For example, the processing component 160 can transmit a denial signal to the clinical system 200.

Figure 5:
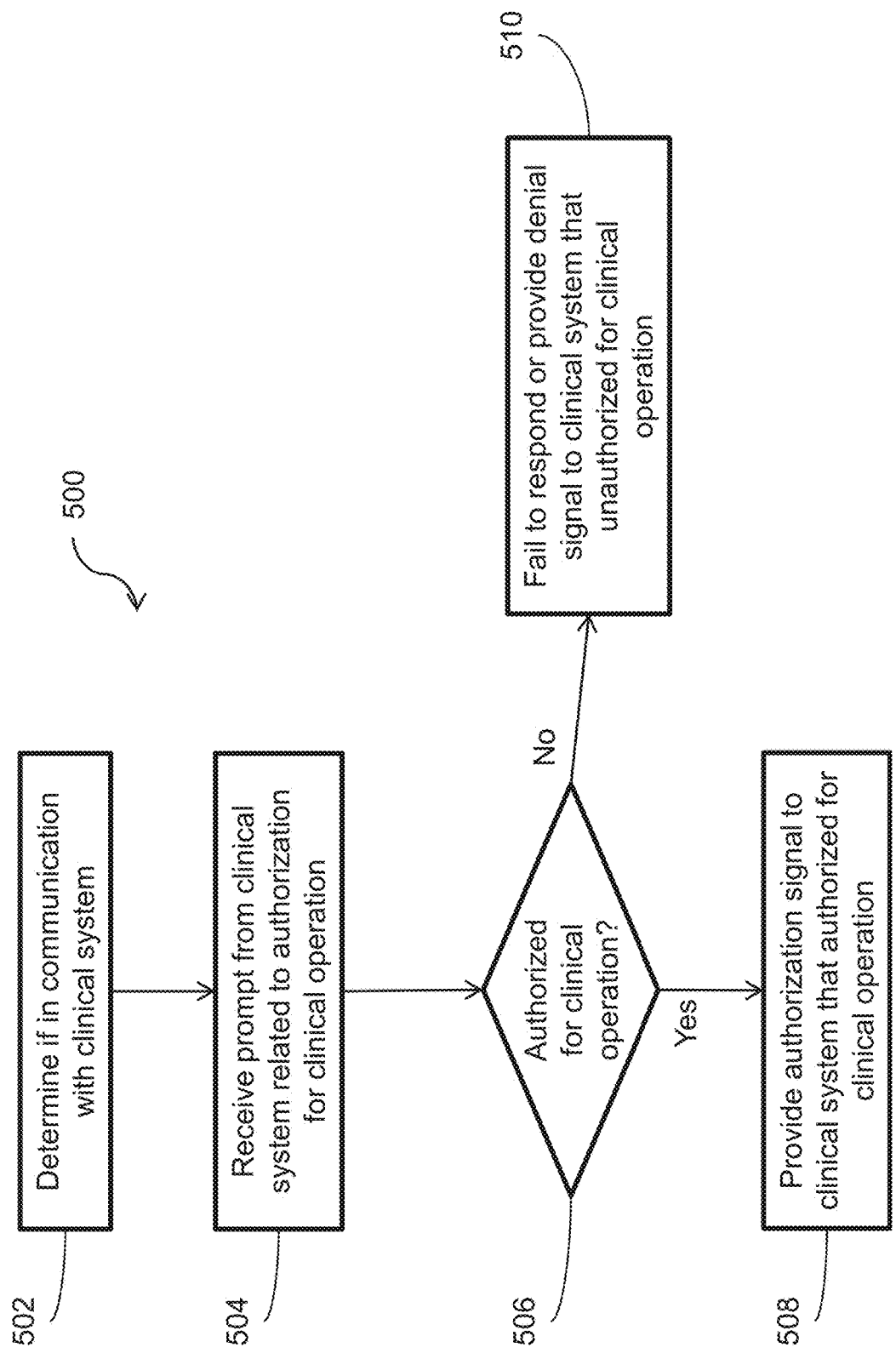
FIG. 5 is a flow diagram of a method of authorizing a limited use intravascular device according to aspects of the present disclosure.

FIG. 5 is a flow diagram of a method 500 of authorizing a limited use intravascular device according to aspects of the present disclosure. One or more steps of the method 500 can be carried out by one or more components of the intravascular device 110, such as the processing component 160. The processing component 160 can use the method 500 to determine if the intravascular device 110 is authorized for clinical operation. The method 500 can be carried out when the intravascular device 110 is brought into communication with the clinical system 200, at various other times while the intravascular device 110 is in communication with the clinical system 200, and/or at various other times while the intravascular device 110 is not in communication with the clinical system 200.

The method 500 can include, at step 502, determining when the intravascular device 110 is in communication with the clinical system 200. For example, the processing component 160 can determine when the connector 150 has been plugged into or otherwise connected the PIM 250 and/or the clinical system 200. In some embodiments, the processing component 160 can determine that the intravascular device 110 is in communication with the clinical system 200 when the clinical system 200 and/or the PIM 250 provide power to the intravascular device 110. In some embodiments, the intravascular device 110 can recognize that the clinical system 200 is reading intravascular device data when the intravascular device 110 is connected to the PIM 250 and/or the clinical system 200.

The method 500 can include, at step 504, receiving a prompt or signal from the clinical system 200. The prompt can be related to the identity of the intravascular device 110 and/or whether the intravascular device 110 is authorized for clinical operation. In some embodiments, the processing component 160 can carry out the self-authentication logic (e.g., step 506) in response to the prompt. In some embodiments, the self-authentication logic is undertaken after the processing component 160 determines that the intravascular device is in communication with the clinical system 200, regardless of whether or not the prompt is received.

The method 500 can include, at step 506, determining if the intravascular device 110 is authorized for clinical operation. In some embodiments, step 506 can be executed by the processing component 160 without allowing the clinical system 200 to access the intravascular device. For example, the processing component 160 alone, or in combination with the memory component 170, can make the determination. That is, the processing component 160 can make the determination using data controlled by the processing component 160 itself (as opposed to the clinical system 200 determining if the intravascular device 110 is authorized based on intravascular device data accessed by the clinical system 200).

In some embodiments, determining if the intravascular device 110 is authorized for clinical operation includes determining if a parameter value of the intravascular device 110 is greater than or less than a threshold value. For example, the threshold value can be representative of a period of time after being connected to a clinical system 200 during which the integrity of data collected the intravascular device 100 is guaranteed by the manufacturer. The parameter value can be representative of an actual elapsed time since the intravascular device 110 and the clinical system 200 have been in communication. For example, the threshold value can be representative of the maximum number of times the intravascular device 110 can be connected to any clinical system 200. This can prevent the intravascular device 110 from being inappropriately used in multiple locations and/or with multiple patients, which presents risk of harm to patients. The parameter value can be representative of the actual number of times the intravascular device 110 has been connected/disconnected from any clinical system 200. For example, the threshold value can be representative a maximum number of times that the efficacy of data collection or therapy delivery is guaranteed by the manufacturer. The parameter value can be representative of the actual number of times the intravascular device 110 has collected data and/or provided therapy. The processing component 160 can determine that the intravascular device 110 is authorized or unauthorized for clinical operation depending on whether the parameter value is greater than or less than the threshold value. The parameter types described herein are exemplary only, and other suitable parameters can be used. Similarly, the threshold check described herein is exemplary only, and other suitable logical checks can be implemented by the processing component 160.

When the intravascular device 110 is authorized for clinical operation, the method 500 includes, at step 508, providing an affirmative response to the clinical system 200. For example, the processing component 160 can transmit an authorization signal representative of the determination that the intravascular device 110 is authorized for clinical operation to the clinical system 200. The method 500 can include, after step 508, providing the clinical system 200 access to intravascular device data stored on the intravascular device 110 for sensing, measuring, and/or therapy. For example, the clinical system 200 can access the memory component 170 to retrieve operating parameters for IVUS imaging. For example, the PIM 250 and/or the clinical system 200 can provide a valid unlock command to change the stated of the connect 150 such that the processing component 160 permits access to the memory component 170. The clinical system 200 can control the intravascular device 110 to perform IVUS imaging using the operating parameters. Communication between the intravascular device 110 and the clinical system 200 can be established such that the clinical system 200 accesses the intravascular device data in the format usable by the clinical system 200.

When the intravascular device 110 is not authorized for clinical operation, the method 500 includes, at step 510, failing to respond to or providing a negative response to the clinical system 200. For example, the processing component 160 can fail to identify itself to the clinical system 200 by not responding to the prompt received from the clinical system 200. In some embodiments, the processing component 160 can stop use of the intravascular device 110. In some embodiments, the clinical system 200 can disallow use of the intravascular device 110 when no response is received to the prompt transmitted by the clinical system 200. For example, the processing component 160 can transmit a denial signal representative of the determination that the intravascular device 110 is unauthorized for clinical operation to the clinical system 200. In response to receiving the denial signal, the clinical system 200 to disallow clinical operation of the intravascular device 110.

In some embodiments, the intravascular device 110 can be properly reprocessed and/or reconditioned by the manufacturer or a third party such that the intravascular device 110 is authorized for reuse. For example, the authentication logic (e.g., the parameter value, the threshold value, etc.) of the processing component 160 can be reset such that it allows the intravascular device 110 to be reused when the authentication logic is executed. For example, the processing component 160 can receive a signal from the clinical system 200 indicating that the intravascular device 110 has been properly reprocessed and/or reconditioned. The signal can be representative of information known only to authorized parties, such as a bona fide purchaser of the intravascular device 110 from the manufacturer or authorized third party, and difficult for an unauthorized third party to have knowledge of. In response to the signal, the processing component 160 can allow clinical operation of and/or access to the intravascular device 110 even when the authentication logic (e.g., step 506) indicated that the intravascular device 110 was unauthorized.

In some embodiments, the intravascular device 110 can receive a manufacturer override signal from the clinical system 220. The override signal can be received when the processing component 160 has determined that the intravascular device 110 is unauthorized for clinical operation. The override signal can reset and/or disable the authentication logic implemented by the processing component 160. The override signal can be representative of secret information known only to the manufacturer, such as unique identifying information (e.g., serial number of the intravascular device 110), that is difficult for an unauthorized third party to have knowledge of without violation of laws, regulations, contracts, etc. For example, the secret information cannot be accessed while the connector 150 is in either an armed state or a locked state. In response to the override signal, the processing component 160 can allow clinical operation of and/or access to the intravascular device 110 even when the authentication logic (e.g., step 506) indicated that the intravascular device 110 was unauthorized. The manufacturer override signal can facilitate critical operations required of the manufacturer, such as testing, investigating product complaints, failures, etc. The override signal can be described as an unlock command to change the state of the connector 150 from a locked state to an unlocked state.

One or more security features can be implemented by the processing component 160 and/or the memory component 170. For example, the processing component 160 can be configured to automatically block access to calibration and identification information stored in the memory component 170 after a predetermined time after the parameter value being tracked has expired (e.g., a use time). For example, the capacity of the charge storage component can be selected such that the life of the charge storage component 180 is less than the time required for the processing component 160 and/or the memory component 170 to be unlocked by brute force attack and/or a priori knowledge of the unlocking method.

Figure 6:
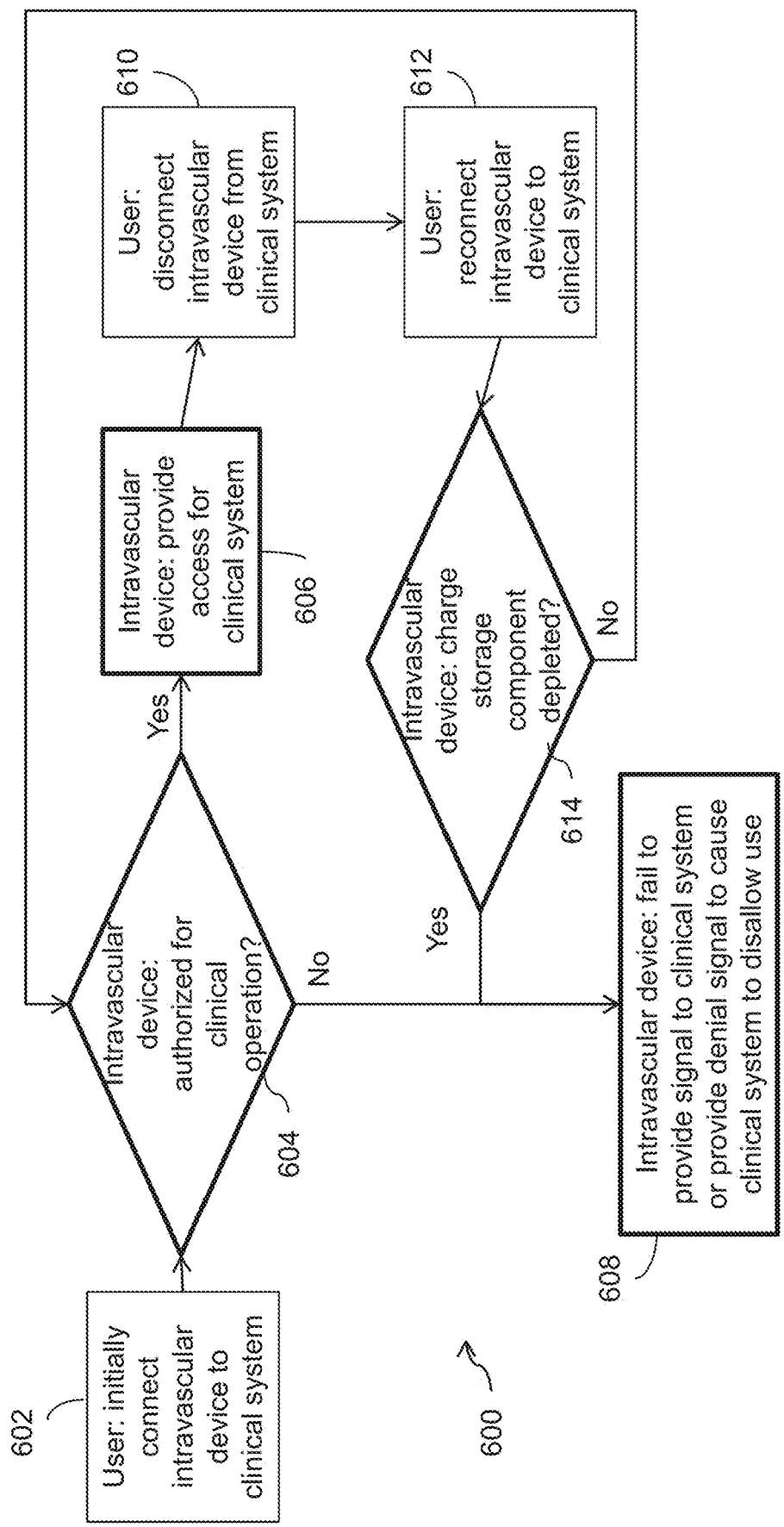
FIG. 6 is a flow diagram of a method of authorizing a limited use intravascular device in an intravascular system according to aspects of the present disclosure.

FIG. 6 is a flow diagram of the method 600 of authorizing the limited use intravascular device 110 in the intravascular system 100 according to aspects of the present disclosure. One or more steps of the method 600 can be carried out by a user in the clinical environment and/or one or more components of the intravascular device 110, such as the processing component 160. The particular parameters and logical tests described with respect to the method 600 are exemplary only. Other suitable parameters and/or logical tests can be implemented in various embodiments.

The method 600 can include, at the step 602, a user initially bringing the intravascular device 110 into communication with the clinical system 200. For example, the user can plug the connector 150 into the PIM 250 and/or the clinical system 200. The method 600 can include, at step 604, the processing component 160 determining if the intravascular device 110 is authorized for clinical operation. The clinical system 200 need not access intravascular device data in step 604. For example, the clinical system 200 does not read data from the memory component 170, and the processing component 160 does not transmit information to the clinical system 200. Step 604 can be similar to the step 506 described above. When the processing component determines that the intravascular device 110 is authorized for clinical operation, the method 600 can include, at step 606, the processing component 160 providing access to the intravascular device 110 for the clinical system 200. For example, the clinical system 200 can access intravascular device data stored on the intravascular device 110 to control the intravascular device 110 for sensing, measuring, and/or applying therapy. When the processing component 160 determines that the intravascular device 110 is unauthorized for clinical operation, the method 600 can include, at step 608, the processing component 160 failing to provide a signal the clinical system 200 or providing a denial signal to the clinical system 200 to cause the clinical system to disallow use of the intravascular device 110.

The method 600 can include, at step 610, the user ending communication between the intravascular device 110 and the clinical system 200. For example, the user can unplug the connector 150 from the PIM 250 and/or the clinical system 200. The connector 150 can be unplugged during the course of a clinical procedure as a routine matter. The method 600 can include, at step 612, the user reestablishing communication between the intravascular device 110 and the clinical system 200. For example, the connecter 150 can be reconnected to the PIM 250 and/or the clinical system 200 after some time to continue using the intravascular device 110, e.g., with the same patient during the same procedure.

The method 600 can include, at step 614, the processing component 160 determining if the charge storage component 180 is depleted. If the charge storage component 180 is depleted, the processing component 160 may no longer be able to implement the self-authentication logic described herein. As a result, continued use of the intravascular device 110 may present risk of harm to the patient if the authenticity of the intravascular device 110 is unable to be verified. The charge storage component 180 can become depleted, e.g., when such time has passed between steps 610 and 612 that it is unlikely that the intravascular device 110 is being used in the same procedure with the same patient. When the charge storage component 180 is depleted, the processing component 160 determining that the intravascular device 110 is unauthorized for use. Thus, the method 600 can include, at step 608, the processing component 160 failing to provide a signal the clinical system 200 or providing a signal to the clinical system 200 to cause the clinical system to disallow use of the intravascular device 110.

When the charge storage component 180 is not depleted, the method 600 can include, at step 604, the processing component 160 determining if the intravascular device 110 is authorized for clinical operation. In some embodiments, determining if the intravascular device 110 is authorized for clinical operation can include determining if the communication between the intravascular device 110 and the clinical system 200 is reestablished within a predetermined threshold. The threshold time can be representative of, for example, the duration of an average procedure. When the connection is reestablished within the threshold time, it is likely that the intravascular device 110 is being used in the same procedure with the same patient. Thus, little risk of harm to the patient exists. The processing component 160 can determine that the intravascular device 110 is authorized for clinical operation, and the method 600 can continue with step 606, as described above. When the connection is reestablished after the threshold time, it is likely that the intravascular device 110 is no longer being used in the same procedure and/or with the same patient. Thus, risk of harm to the patient is present if the intravascular device 110 is used further. The processing component 160 can determine that the intravascular is unauthorized for clinical operation, and the method 600 can continue with step 608, as described above. In some embodiments, the intravascular device 110 can be disconnected and reconnected to the clinical system 200 multiple times within the threshold time. In some embodiments, an additional threshold can limit the number of times the intravascular device 110 is disconnected and reconnected clinical system 200 within the threshold time.

The processing component 160 can maintain the elapsed time since the intravascular device 110 was initially brought into communication with the clinical system 200 (step 602), even when the intravascular device 110 is disconnected from the clinical system 200. As described above, the charge storage component 180 can power the processing component 160 and/or the memory component 170 when the intravascular device 110 is not being powered by the PIM 250 and/or the clinical system 200. In some embodiments, the processing component 160 can determine if the charge storage component 180 is depleted after a predetermined time, even when intravascular device 110 is not in communication from the clinical system 200. For example, step 614 can be carried out a predetermined time after the intravascular device 110 was initially connected to the clinical system 200 (step 602) and/or after the intravascular device 110 was disconnected from the clinical system 200 (step 610), regardless of whether the intravascular device 110 has been reconnected to the clinical system 200 (step 612). Similarly, the processing component can determine that if intravascular device 110 is authorized for clinical operation (step 604), even when the intravascular device 110 is not in communication with the clinical system 200. For example, step 604 can be carried out after the processing component 160 determines that the charge storage component 180 has been depleted, while the intravascular device 110 is disconnected from the clinical system 200. When the charge storage component 180 is depleted, the processing component 160 can determine that the intravascular device 110 is authorized for clinical operation, while the intravascular device 110 is not in communication with the clinical system 200. When the intravascular device 110 is next in communication with the clinical system, the processing component 160 can transmit a denial signal to the clinical system 200 representative of the determination that the intravascular device 110 is unauthorized for clinical operation. In response, the clinical system 200 can disallow clinical operation of the intravascular device 110.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

While the present disclosure referred to primarily to intravascular devices, the system disclosed herein is well suited to authentication of any disposable or limited use medical device. For example, the teachings of the present disclosure can be implemented in transluminal and/or endoscopic devices. One skilled in the art will recognize the application of the principles herein across other disciplines.

What is claimed is:

1. An intravascular system, comprising:
a limited use intravascular device comprising a flexible elongate member having a sensing component at a distal portion and a connector at a proximal portion, the intravascular device further including:
a memory component configured to store a parameter value;
a processing component configured to determine if the intravascular device is authorized for clinical use based on the parameter value; and
a charge storage component configured to power at least one of the memory component and the processing component;
a clinical system comprising a computing device in direct or indirect communication with the intravascular device;
wherein the processing component, in response to determining that the intravascular device is in communication with the clinical system, is configured to determine if the intravascular device is authorized for clinical operation while the memory component is in a first state in which the clinical system is disallowed access to the memory component; and wherein the clinical system is configured to allow or disallow the clinical operation of the intravascular device in response to a signal received from the intravascular device representative of a determination by the processing component as to whether the intravascular device is authorized for clinical operation.

2. The intravascular system of claim 1, wherein the processing component is configured to determine if the intravascular device is authorized for clinical operation by determining if the parameter value of the intravascular device is greater than or less than a threshold value.

3. The intravascular system of claim 2, wherein the memory component is configured to track the parameter value with the intravascular device while the intravascular device is not in communication with the clinical system.

4. The intravascular system of claim 3, wherein the intravascular device is configured to track the parameter value by providing power to at least one of the processing component and the memory component of the intravascular device using the charge storage component of the intravascular device while the intravascular device is not in communication with the clinical system.

5. The intravascular system of claim 4, wherein the processing component is configured to:
determine that the intravascular device is unauthorized for clinical operation based on the tracked parameter value while the intravascular device is not in communication with the clinical system; and
provide, when the intravascular device is in communication with the clinical system, a denial signal to the clinical system representative of the determination that the intravascular device is unauthorized for clinical operation such that the clinical system disallows clinical operation of the intravascular device.

6. The intravascular system of claim 2, wherein:
the connector is configured to provide direct or indirect communication with the clinical system.

7. The intravascular system of claim 2, wherein the parameter value is representative of at least one of:
an elapsed time since commencement of communication of the intravascular device with any clinical system;
whether the intravascular device has been in communication with any clinical system;
a number of times the intravascular device has been in communication with any clinical system; and
a number of times the intravascular device has collected data and/or provided therapy.

8. The intravascular system of claim 2, wherein the parameter value is stored in the memory component of the intravascular device.

9. The intravascular system of claim 1, wherein processing component is configured to:
receive a prompt from the clinical system to determine if the intravascular device is authorized for clinical operation.

10. The intravascular system of claim 9, wherein the processing component is configured to:
fail to respond to the prompt when it is determined that the intravascular device is unauthorized for clinical operation such that the clinical system disallows clinical operation of the intravascular device.

11. The intravascular system of claim 1, further comprising:
a patient interface module in communication with the intravascular device and the clinical system.

12. The intravascular system of claim 1, wherein the intravascular device is at least one of a catheter or a guide wire.

13. The intravascular system of claim 1, wherein the sensing component is at least one of a intravascular ultrasound (IVUS) imaging component, an optical coherence tomography (OCT) imaging component, a pressure-sensing component, or a flow-sensing component.

14. The intravascular system of claim 1, wherein the processing component is configured to:
provide an authorization signal to the clinical system when it is determined that the intravascular device is authorized for clinical operation.

15. The intravascular system of claim 1, wherein the processing component is configured to:
provide the clinical system access to the memory component of the intravascular device when it is determined that the intravascular device is authorized for clinical operation.

16. The intravascular system of claim 1, wherein the processing component is configured to:
provide a denial signal to the clinical system when it is determined that the intravascular device is unauthorized for clinical operation such that the clinical system disallows clinical operation of the intravascular device.

17. The intravascular system of claim 1, wherein the processing component is configured to determine if the intravascular device is communication with the clinical system by determining if the intravascular device is receiving power from the clinical system.

18. The intravascular system of claim 1, wherein the processing component is configured to access the memory component to determine if the intravascular device is authorized for clinical operation.

19. The intravascular system of claim 1, wherein the processing component is configured to:
receive an override signal from the clinical system when it is determined that the intravascular device is unauthorized for clinical operation; and
provide the clinical system access to intravascular device data stored on the intravascular device.

20. The intravascular system of claim 1, wherein the processing component, in response to receiving a signal indicating that the intravascular device is authorized for clinical operation, is configured to change the memory component to a second state in which the clinical system is allowed access to the memory component.

* * * * *